United States Patent

Kimura et al.

(10) Patent No.: US 6,949,526 B2
(45) Date of Patent: Sep. 27, 2005

(54) ERECTILE DYSFUNCTION REMEDIES CONTAINING PROSTAGLANDIN DERIVATIVES AS THE ACTIVE INGREDIENT

(75) Inventors: Kazunori Kimura, Takamatsu (JP); Masami Narita, Mishima-gun (JP); Kozo Yoshida, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 183 days.

(21) Appl. No.: 10/333,242

(22) PCT Filed: Jul. 30, 2001

(86) PCT No.: PCT/JP01/06540

§ 371 (c)(1),
(2), (4) Date: Jan. 16, 2003

(87) PCT Pub. No.: WO02/09717

PCT Pub. Date: Feb. 7, 2002

(65) Prior Publication Data

US 2004/0002477 A1 Jan. 1, 2004

(30) Foreign Application Priority Data

Jul. 31, 2000 (JP) ........................................ 2000-230149

(51) Int. Cl.$^7$ ........................ A61K 31/70; A61K 31/557
(52) U.S. Cl. .......................................... 514/58; 514/573
(58) Field of Search .................................... 514/58, 573

(56) References Cited

U.S. PATENT DOCUMENTS 5,942,545 A * 8/1999 Samour et al. ............. 514/573

FOREIGN PATENT DOCUMENTS

| EP | 860430 A2 | 8/1998 |
| EP | 0 860 430 A2 * | 8/1998 |
| WO | WO 93/00894 A1 | 1/1993 |

* cited by examiner

Primary Examiner—Elli Peselev
(74) Attorney, Agent, or Firm—Sughrue Mion, PLLC

(57) ABSTRACT

Therapeutic agents for erectile dysfunction containing as the active ingredient prostaglandin derivatives of formula (I)

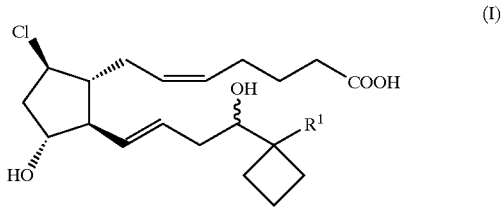

(wherein, $R^1$ is ethyl or n-2-propenyl.), esters thereof, non-toxic salts thereof, or cyclodextrin clathrate compounds thereof.

The compounds of the formula (I) are useful for the treatment of erectile dysfunction.

3 Claims, No Drawings

ERECTILE DYSFUNCTION REMEDIES CONTAINING PROSTAGLANDIN DERIVATIVES AS THE ACTIVE INGREDIENT

TECHNICAL FIELD

The present invention relates to a therapeutic agent for erectile dysfunction. More particularly, it relates to a therapeutic agent for erectile dysfunction containing as the active ingredient prostaglandin derivatives of the formula (I)

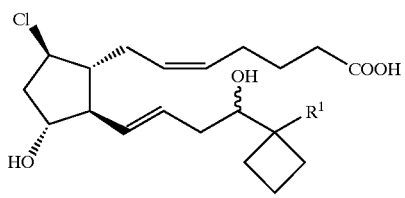

(I)

(wherein, $R^1$ is ethyl or n-2-propenyl.), esters thereof, nontoxic salts thereof or cyclodextrin clathrate compounds thereof.

BACKGROUND ART

Male sexual dysfunction, in particular erectile dysfunction, is attributed to various causes such as aging, operation of prostate gland, injury of nerve cord, and diabetes. However, what is common in these causes is that a decrease of blood flow into the corpus cavernosum penis is the direct cause. As one of methods of treating it, administration of a vasodilator such as prostaglandin $E_1$ (hereinafter abbreviated as $PGE_1$) has been considered effective (DICP—The animal of Pharmacotherapy, 5, 363 (1991)). However, $PGE_1$ has problems that it is attended with pain (angialgia) upon administration, that the drug itself is unstable and so forth.

On the other hand, it has been found that prostaglandin $E_2$ (hereinafter, abbreviated as $PGE_2$) that has oxytocic effect also has utillity for erectile dysfunction. This has made it unclear whether or not the erectile dysfunction improving action of $PGE_1$ is simply based on its vasodilating action (WO93/00894).

$PGE_2$ is known to be as a metabolite in the cascade of arachidonic acid and have various activities such as cytoprotection, oxytocic effect, algesic effect, promotion of vermicular movement of digestive tract, arousal effect, supression of gastric-acid secretion, hypotensive activity, and diuretic action.

Studies in recent years have revealed that $PGE_2$ receptores have subtypes that play different roles from each other. Currently known subtypes are roughly classified into four groups called $EP_1$, $EP_2$, $EP_3$, and $EP_4$, respectively (Negishi M. et al, J. Lipid Mediators Cell Signaling 12, 379–391 (1995)). Examination of separate roles of these receptors with compounds that bind to specific receptors and finding compounds not to bind any other subtype receptors has made it possible to obtain drugs having less side effects.

Recently, an application disclosing that the compounds having an ω-chain of $PGE_2$ modified with a hydroxyl group have an effect on erectile dysfunction equivalent to that of $PGE_1$ and are less irritating has been laid open to public inspection. It also describes that the compounds disclosed therein are $EP_2$-specific (cf., WO99/02164).

Furthermore, the compounds used in the present invention represented by the formula (I) are the compounds described in Example 17 and 17(1) in the specification of Europian Patent Publication No. 860430.

SUMMARY OF THE INVENTION

The inventors of the present invention have made extensive study with a view to finding compounds that have erectile dysfunction improving effect equivalent to or higher than $PGE_1$ and 19-hydroxy-$PGE_2$ and have less side effects. As a result, they have found that the compounds used in the present invention of the formula (I) meet the object and attained the present invention.

The compounds used in the present invention specifically bind to subtype $EP_2$ receptor but do not almost bind to other subtypes $EP_1$, $EP_3$, $EP_4$ and the like. Therefore, the compounds used in the present invention do not have algesic action which may be attributed to $EP_1$, oxytocic action which may be attributed to $EP_3$, immunoregulation effect which may be attributed to $EP_4$, and the like and hence they are drugs free of influences on these actions. In addition, as will be apparent from the experiments shown hereinbelow, the compounds used in the present invention exhibit effects equivalent to those of $PGE_1$ and 19-Hydroxy-$PGE_2$ whose usefulness has already been recognized, so that they are useful as therapeutic agents for erectile dysfunction having less side effects. Furthermore, the compounds used in the present invention are applicable to improving of female sexual function. Although the compounds used in the present invention of the formula (I) are specifically disclosed in the specification of Europian Patent Publication No. 860430, it has not been known that the compounds are effective to erectile dysfunction and this is the first time that it was found.

DISCLOSURE OF THE INVENTION

The present invention relates to a therapeutic agent for erectile dysfunction. More particularly, it relates to a therapeutic agent for erectile dysfunction containing as the active ingredient one or more compounds selected from prostaglandin derivatives of the formula (I)

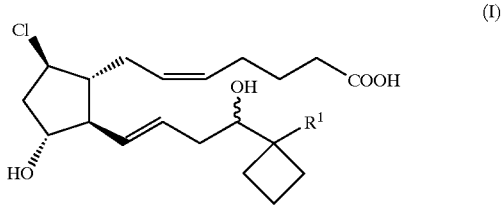

(I)

(wherein, $R^1$ is ethyl or n-2-propenyl.), nontoxic salts thereof or cyclodextrin clathrate compounds thereof.

[Esters]

The compounds used in the present invention of the formula (I) can be converted into esters by a known method. Since esterification increases stability and absorbability of the compounds, the esters are useful as pharmaceutical preparations. Preferred esters include alkyl esters. C1–4-Alkyl esters are more preferred, with methyl ester being most preferred.

[Salts]

The compounds used in the present invention of the formula (I) can be converted into corresponding salts by a known method. The salts are preferably nontoxic and water-soluble salts. Suitable salts include alkali metal (potassium, sodium, etc.) salts, alkaline earth metal (calcium, magnesium, etc.) salts, ammonium salts, and pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine, etc.) salts. Preferred salts include lysine salts. In addition, the compounds used in the present invention of the formula (I) can be converted into hydrates by a known method.

[Clathrate Compounds]

The compounds used in the present invention of the formula (I) or esters thereof can be converted into cyclodextrin clathrate compounds by the method described in the specifications of GB 1,351,238 or GB 1,419,221 by using α-, β- or γ-cyclodextrin or mixtures thereof. Since conversion into cyclodextrin clathrate compounds increases stability and solubility in water of the compounds, the cyclodextrin clathrate compounds are convenient when they are used as drugs.

[The Method for the Preparation of Compounds of the Formula (I)]

The compounds used in the present invention of the formula (I), esters thereof or nontoxic salts thereof can be prepared by the method described in the specification of Europian Patent Publication No. 860430.

BEST MODE FOR CARRYING OUT THE INVENTION

That the compounds used in the present invention of the formula (I) can be used for the therapy of erectile dysfunction was confirmed by the following pharmacological experiments.

EXAMPLE 1

Corpus Cavernosum Relaxation Activity in Cats

[Pharmacological Examination]

Under anesthesia with urethane, penis of five cats (hybrid, weight about 3.5 kg) was removed. In the krebs solution, a corpus cavernosum was isorated, quartered and suspended with the tention of 200 mg in the Magnus tube. 10 $\mu$M norepinephrine was added and the tissue was constricted. Then the stable contraction was checked. After the addition of norepinephrine, (5Z, 9β, 11α, 13E)-17,17-propano-11,16-dihydroxy-9-chloro-20-norprosta-5,13-dienic acid.lysine salt (compound A) and (5Z, 9β, 11α, 13E)-17,17-propano-11,16-dihydroxy-9-chloroprosta-5,13,19-trienic acid (compound B), which are the compounds of the formula (I), were added respectively and the changes of the contraction were measured. As controls, $PGE_1$ and 19-hydroxy-$PGE_2$ were used. Each compounds were disolved in DMSO and used. The contraction induced by 10 $\mu$M norepinephrine was considered as 100% and the percentages of the relaxation rate were calculated. These results were showed on Table 1.

TABLE 1

| Adominstered Compounds | Dose ($\mu$M) | Corpus cavernosum relaxation rate (%) |
|---|---|---|
| Compound A | 0.1 | 26.8 ± 4.2 |
| Compound A | 1.0 | 35.2 ± 2.8 |
| Compound B | 0.1 | 18.1 ± 4.8 |
| Compound B | 1.0 | 36.8 ± 4.2 |

TABLE 1-continued

| Adominstered Compounds | Dose ($\mu$M) | Corpus cavernosum relaxation rate (%) |
|---|---|---|
| $PGE_1$ | 0.1 | 21.3 ± 2.3 |
| $PGE_1$ | 1.0 | 35.5 ± 5.0 |
| 19-hydroxy-$PGE_2$ | 0.3 | 20.0 ± 4.2 |
| 19-hydroxy-$PGE_2$ | 1.0 | 27.2 ± 4.7 |

Numeric values are Means ± SE.

[Consideration]

The compounds used in the present invention of the formula (I) (compound A and B) elicited dose-dependent relaxasions of corpus cavernosum and its intensity were at the same level as $PGE_1$. The contraction activity of the compounds used in the present invention of the formula (I) (compound A and B) were 3 or 10 times as potent as that of 19-hydroxy-$PGE_2$.

EXAMPLE 2

Corpus Cavernosum Relaxation Activity in Human

[Pharmacological Examination]

The samples of the human corpus cavernosum taken at the time of operative treatment in agreement of the patient were suspended with the tention of 500 mg in the Magnus tube fulled by glucose-added Krebs buffer. The $10^{-5}$M (10 $\mu$M) noradrenalin-induced contraction reaction, acetylcholine-induced relaxation reaction and electrostimulation(EFS)-induced contraction reaction were checked and the samples responded normaly were used in the experiment. It was reconstricted by 10 $\mu$M noradrenalin, the compound A used in the present invention of the formula (I) (n=4), the compound B used in the present invention of the formula (I) (n=5) or PGE1 (n=5), which were disolved by DMSO, were added cumulatively and the relaxation reacton was recorded on the chart. The contraction induced by 10 $\mu$M noradrenaline was concidered as 100% and the percentage of the relaxation rate was calculated. These results were showed on Table 2.

TABLE 2

| Adominstered Compounds | Dose ($\mu$M) | Corpus cavernosum relaxation rate (%) |
|---|---|---|
| compound A | 1.0 | 29.9 ± 13.7 |
| compound A | 10 | 44.5 ± 12.6 |
| compound B | 1.0 | 25.0 ± 4.4 |
| compound B | 10 | 45.3 ± 4.5 |
| $PGE_1$ | 1.0 | 16.8 ± 7.2 |
| $PGE_1$ | 10 | 27.9 ± 8.8 |

Numeric values are Means ± SE.

[Consideration]

In human corpus carvenosum, the activity of compound A and B used in the present invention of the formula (I) were 1.6 times as potent as that of $PGE_1$, so they are useful for the treatment of erectile dysfunction.

[Toxicity]

It has been confirmed that the compounds used in the present invention of the formula (I) have sufficiently low toxicity and are sufficiently safe for use as pharmaceutical preparations. For example, the maximal tolerated dose of the compound A (lysine salts) in the compound of the formula (I) was 30 mg/kg weight or more for rat intravenous administration.

INDUSTRIAL APPLICABILITY

The compounds used in the present invention of the formula (I) are useful for the treatment of erectile dysfunction. When used for the above-mentioned purposes, usually the compounds used in the present invention of the formula (I), esters thereof, nontoxic salts thereof, and cyclodextrin clathrate compounds thereof are locally administered in parenteral forms. Use of them in the form of prodrug provides advantages such as elimination of irritation, improved absorption, improved stability and the like.

The doses to be administered are determined depending upon age, body weight, symptom, the desired therapeutic effect, the route of administration, and the duration of the treatment etc. In the human adult, the doses per person are generally from 1 µg to 100 mg, by oral administration, from once up to several times per day, and from 0.1 µg to 10 mg, by parenteral administration (preferably, percutaneous administration, subcutaneous administration, perurethral administration, or intravenous administration) from once up to several times per day, or by continuous administration for from 1 hour to 24 hours per day into vein.

Of course, as described above, the dose may vary depending on various conditions, and in some cases an amount less than the amount described above will suffice or in some cases, administration of an amount exceeding the above-mentioned range will be necessary.

When the compounds used in the present invention of the formula (I) are administered, they are used in the form of injection, external preparations such as ointments, patches for attaching to skin, suppositories and the like for parenteral administration.

The injection for parenteral administration according to the present invention includes sterile aqueous or nonaqueous solutions, suspensions and emulsions. The aqueous solutions and suspensions include, for example, distilled water for injection and saline. The nonaqueous solutions and suspensions include, for example, propylene glycol, polyethylene glycol and plant oils such as olive oil, alcohols such as ethanol, Polysorbate 80 (registered trademark) and the like. Such compositions may further contain antiseptics, humectants, emulsifiers, dispersants, stabilizers, or auxiliaries such as dissolution auxiliaries (for example, glutamic acid and aspartic acid). These can be sterilized by filtration through a bacteria-retaining filter, compounding of a germicide, or irradiation. These can be sterilized by producing a sterile solid composition and sterilizing before use or they are dissolved in sterile distilled water for injection or other solvents before they can be used.

Other compositions for parenteral administration in dude external liquids, ointments, liniments, patches, and suppositories, each containing one or more active ingredients.

The ointment may contain besides a base such as white vaseline, pH adjusters, surfactants, antiseptics, emulsifiers, dispersants, stabilizers, dissolution auxiliaries and so forth.

PREPARATION EXAMPLE 1

Freeze-dried Products

After mixing the following components by a conventional method, the resulting solution was sterilized by a conventional method and 1 ml portions thereof were filled in vials, respectively, and freeze-dried by a conventional method to obtain 100 vials of injection containing each 0.2 mg of the active ingredient.

| | |
|---|---|
| (5Z,9β,11α,13E)-17,17-propano-11,16-dihydroxy-9-chloro-20-norprosta-5,13-dienic acid · lysine salt | 27.3 mg |
| Mannitol | 5 g |
| Distilled water | 100 ml |

PREPARATION EXAMPLE 2

Ointment

The following components were mixed by a conventional method and 10 g portions thereof were filled in tubes, respectively, to obtain 100 tubes of ointment containing each 0.2 mg per 1 g of the active ingredient.

| | |
|---|---|
| (5Z,9β,11α,13E)-17,17-propano-11,16-dihydroxy-9-chloro-20-norprosta-5,13-dienic acid · lysine salt | 273 mg |
| White vaseline | 1 kg |

What is claimed is:

1. A method for treating erectile dysfunction, which comprises administering to a subject in need thereof an effective amount of one or more compounds selected from the group consisting of prostaglandin compounds of the formula (I):

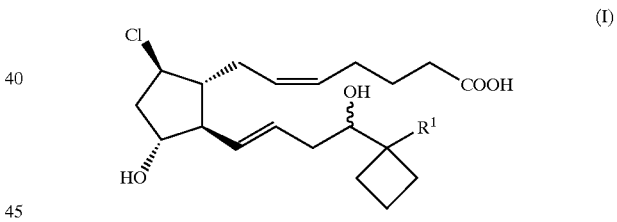

wherein, $R^1$ is ethyl or n-2-propenyl, esters thereof, nontoxic salts thereof and cyclodextrin clathrate compounds thereof.

2. The method as claimed in claim 1, wherein (5Z,9β,11α,13E)-17,17-propano-11,16-dihydroxy-9-chloro-20-norprosta-5,13-dienic acid, a lysine salt thereof, or a α-cyclodextrin clathrate compound thereof is administered.

3. The method as claimed in claim 1, wherein (5Z,9β,11α,13E)-17,17-propano-11,16-dihydroxy-9-chloroprosta-5,13,19-trienic acid, a lysine salt thereof, or a α-cyclodextrin clathrate compound thereof is administered.

* * * * *